United States Patent [19]

Miyanaga et al.

[11] Patent Number: 5,150,702
[45] Date of Patent: Sep. 29, 1992

[54] IRIS DIAPHRAGM DEVICE AND ENDOSCOPE HAVING THE SAME

[75] Inventors: Hirofumi Miyanaga; Nobuyuki Sakamoto; Koichi Yoshimitsu, all of Tokyo; Yasundo Tanaka, Urawa, all of Japan

[73] Assignee: Olympus Optical Co., Ltd., Tokyo, Japan

[21] Appl. No.: 677,191

[22] Filed: Mar. 29, 1991

[30] Foreign Application Priority Data

Jun. 18, 1990 [JP] Japan .................................. 2-160485
Jan. 17, 1991 [JP] Japan .................................... 3-4019

[51] Int. Cl.⁵ .......................... A61B 1/06; G03B 9/02; H04N 5/238
[52] U.S. Cl. ........................ 128/6; 358/228; 354/62; 354/453; 354/271.1
[58] Field of Search .................. 128/4, 5, 6; 358/228, 358/210; 354/62, 453, 446, 271.1, 270, 274

[56] References Cited

U.S. PATENT DOCUMENTS

| | | | |
|---|---|---|---|
| 3,817,635 | 6/1974 | Kawahara | 128/6 |
| 4,086,605 | 4/1978 | Ishikawa et al. | 354/270 |
| 4,300,167 | 11/1981 | Miller et al. | 358/210 |
| 4,425,599 | 1/1984 | Rieder et al. | 128/6 |
| 4,734,777 | 3/1988 | Okino et al. | 358/228 |
| 4,737,855 | 4/1988 | Arai et al. | 358/228 |
| 4,873,572 | 10/1989 | Miyazaki et al. | 128/6 |
| 4,884,557 | 12/1989 | Takehana et al. | 128/4 |
| 4,930,494 | 6/1990 | Takehana et al. | 128/4 |
| 4,963,916 | 10/1990 | Tanaka et al. | 354/435 |
| 4,977,886 | 12/1990 | Takehana et al. | 128/4 |
| 4,987,314 | 1/1991 | Gotanda et al. | 250/551 |
| 4,999,664 | 3/1991 | Foust | 354/446 |
| 5,008,699 | 4/1991 | Tominaga et al. | 354/435 |

*Primary Examiner*—John G. Weiss
*Attorney, Agent, or Firm*—Armstrong & Kubovcik

[57] ABSTRACT

A diaphragm blade is rotatably secured by a rotational shaft disposed in a base. The aperture blade has a diaphragm aperture at the central portion thereof. A shape-memory alloy which deforms in accordance with temperatures and an elastic member are respectively secured to the end portions of the aperture blade. The other end portion of each of the shape-memory alloy and the elastic member is secured to the base. The shape of the shape-memory alloy is deformed by changing the temperature so that the aperture blade is displaced. In consequence, a diaphragm aperture formed in the aperture blade is positioned/retracted from the optical path so as to change the quantity of light which is transmitted through the optical path.

27 Claims, 13 Drawing Sheets

IRIS DIAPHRAGM DEVICE AND ENDOSCOPE HAVING THE SAME

BACKGROUND OF THE INVENTION

1. Field of the Invention

The present invention relates to an improvement in an operating mechanism of an iris diaphragm device.

2. Description of the Prior Art

Recently, there have been widely used endoscopes which are capable of observing the organ in the cavity or the like by inserting its elongated insertion portion into the cavity and, if necessary, performing a variety of medical curing operations by using a selected curing device in such a manner that the curing device is inserted into a channel formed in the endoscope.

When the endoscope is used to observe the organ or the like, the quantity of irradiating light or the quantity of light received by the observing means is automatically adjusted so that a subject image of a proper brightness level is always be obtained. As a means for adjusting the quantity of light, a mechanical iris diaphragm device for adjusting the quantity of irradiating light is usually employed in a light source device for supplying irradiating light to the endoscope. However, it might by considered feasible to employ a structure which is arranged in such a manner that a mechanical iris diaphragm device for adjusting the quantity of irradiating light or the quantity of light received by the observing means is disposed at the front portion of the insertion portion of the endoscope.

The mechanical iris diaphragm device is, as disclosed in Japanese Patent Publication No. 1986-54779, operated in such a manner that an electric motor serving as an operating means is rotated so as to operate aperture blades via a transmission mechanism such as a gear. Furthermore, a mechanism arranged in such a manner that the aperture blades are operated by an electromagnet serving as the operating means has been disclosed in Japanese Patent Publication No. 1981-9692. In addition, another structure arranged in such a manner that a bimorph device is used as the operating means has been disclosed in Japanese Utility Model Publication No. 1989-88930.

However, the structure of the iris diaphragm device becomes too complicated in the case where the electric motor or the electromagnet is employed as the operating device for the iris diaphragm device. Therefore, the size of the iris diaphragm device cannot be sufficiently reduced so as to have the iris diaphragm device included in the front portion of the insertion portion of the endoscope. Since the bimorph device employed as the operating means for the iris diaphragm device as disclosed in Japanese Utility Model Publication No. 1989-88930 cannot sufficiently displace the aperture blades, a transmission mechanism for enlarging the quantity of displacement is necessary to be provided between the bimorph device and the aperture blades. Therefore, also the size of the iris diaphragm device cannot be reduced satisfactorily.

SUMMARY OF THE INVENTION

An object of the present invention is to provide an iris diaphragm device the overall size of which can be reduced because the structure of a mechanism for displaying an iris diaphragm means can be simplified.

Another object of the present invention is to provide an iris diaphragm device the size of which can be reduced since it is constituted in such a manner that no transmission mechanism is interposed between an iris diaphragm means and an operating means for displacing the iris diaphragm means, the iris diaphragm device being thereby capable of being placed in a small space such as the front portion of the insertion portion of the endoscope.

A further object of the present invention is to provide an endoscope in which the structure of a mechanism for operating an iris diaphragm device can be simplified and thereby the size of the iris diaphragm device can be reduced so that the diameter of the front portion of the insertion portion of the endoscope can be reduced.

An iris diaphragm device according to the present invention comprises: iris diaphragm means which is displaced so as to change the diameter of a diaphragm aperture; operating means including a shape-memory material which is deformed in accordance with temperatures, so as to displace the iris diaphragm means; and temperature changing means for changing the temperature of the shape-memory material of the operating means.

An endoscope according to the present invention comprises: a holding portion disposed adjacent to an operator; an elongated insertion portion extending in front of the holding portion; an iris diaphragm device including an objective optical system disposed at the front portion of the insertion portion and arranged to image incidental light beams, iris diaphragm means which is disposed on the optical path of the objective optical system and which is deformed so as to change the diameter of a diaphragm aperture and operating means having a shape-memory material which is deformed in accordance with temperature so as to displace the iris diaphragm means; and temperature control means for controlling the temperature of the shape-memory material.

Other and further objects, features and advantages of the invention will be appear more fully from the following description.

BRIEF DESCRIPTION OF THE DRAWINGS

FIG. 1 illustrates the structure of a front portion of an insertion portion of an endoscope;

FIG. 2 is a cross sectional view taken along line A—A' of FIG. 1 and illustrating a state where a diaphragm aperture is retracted from an observing optical system;

FIG. 3 is a cross sectional view taken along line A—A' of FIG. 1 and illustrates a state where a diaphragm aperture is aligned with the observing optical system;

FIG. 4 illustrates the overall body of an endoscope;

FIG. 5 is a block diagram which illustrates the structure of the endoscope;

FIG. 6 is a front elevational view which illustrates an operation portion of the endoscope;

FIG. 7 illustrates a second embodiment of an iris diaphragm device according to the present invention;

FIG. 8 illustrates a third embodiment of the iris diaphragm device according to the present invention;

FIGS. 9 and 10 respectively illustrate a fourth embodiment of the present invention, where FIG. 9 is a front elevational view which illustrates the iris diaphragm device, and FIG. 10 is a cross sectional view taken along line G—G' of FIG. 9;

FIGS. 11 to 16 respectively illustrate a fifth embodiment of the present invention, where FIG. 11 is a front elevational view which illustrates a state where a diaphragm aperture of the iris diaphragm device is opened;

FIG. 12 is a front elevational view which illustrates a state where the diaphragm aperture of the iris diaphragm device is closed;

FIG. 13 is a cross sectional view taken along line B—B' of FIG. 11;

FIG. 14 is a cross sectional view taken along line C—C' of FIG. 11;

FIG. 15 illustrates a shape-memory alloy;

FIG. 16 illustrates the configuration of aperture blades;

FIG. 17 is a cross sectional view which illustrates a sixth embodiment of the iris diaphragm device;

FIGS. 18 and 19 respectively illustrate a seventh embodiment of the present invention, where FIG. 18 is a cross sectional view which illustrates the iris diaphragm device;

FIG. 19 illustrates the relationship between the operation of a restoring spring and that of a shape-memory alloy;

FIGS. 20 to 23 respectively illustrate an eighth embodiment of the present invention, where FIG. 20 is a front elevational view which illustrates a state where a diaphragm aperture of the iris diaphragm device is opened;

FIG. 21 is a front elevational view which illustrates a state where the diaphragm aperture of the iris diaphragm device is closed;

FIG. 22 is a cross sectional view taken along line C—C' of FIG. 20; and

FIG. 23 illustrates the relationship between the shape-memory alloy and the restoring spring shown in FIG. 20.

DESCRIPTION OF THE PREFERRED EMBODIMENTS

Figure 4:
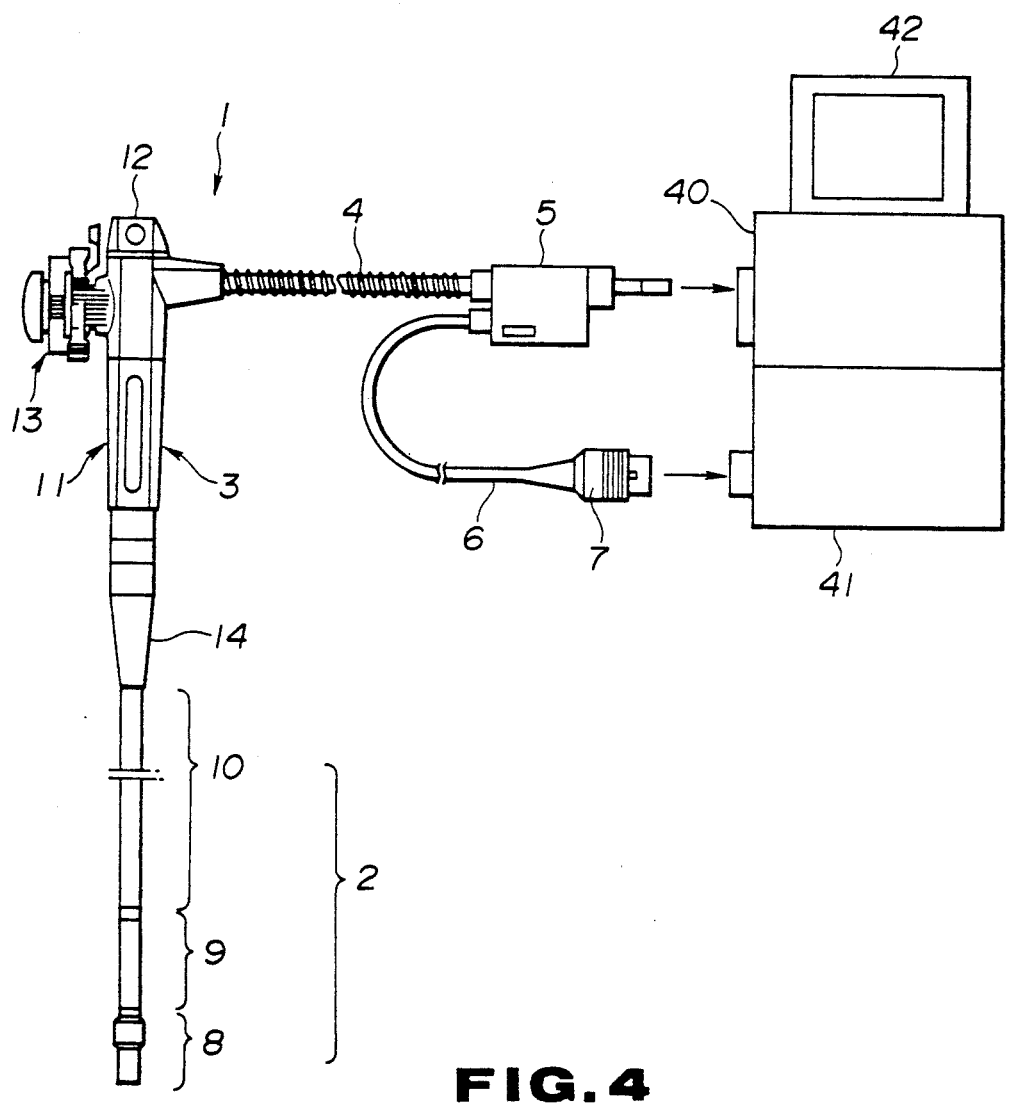

As shown in FIG. 4, an endoscope apparatus comprises an endoscope 1, a light source device 40, a camera control unit (abbreviated to a "CCU" hereinafter) 41 connected to the endoscope 1 and a monitor 42 connected to the CCU 41.

The endoscope 1 has an insertion portion 2 in the form of an elongated shape and having flexibility, an operation portion 3 connected the rear end portion of the insertion portion 2 via a stopper portion 14 and a universal cord 4 extending from the operation portion 3. The universal cord 4 has, an end portion thereof, an LG connector 5 which can be attached/detached to and from the light source device 40. A CCU cable 6 is extended from the LG connector 5, the CCU cable 6 having, at an end portion thereof, a CCU connector 7 which can be attached/detached to and from the CCU 41.

The above-described insertion portion 2 is composed of, when viewed from the front portion, a hard front portion 8, a bending portion 9 which can freely be bent and a soft portion 10. The operating portion 3 comprises a holding portion 11 adjacent to the insertion portion 2 and a switch portion 12 disposed opposite to the insertion portion 2. The holding portion 11 has two side surfaces confronting each other, one of the two confronting side surfaces having a bending operation knob 13 for controlling bending of the bending portion 9.

Furthermore, the above-described universal cord 4 is extended from another side surface of the holding portion 11.

Figure 1:
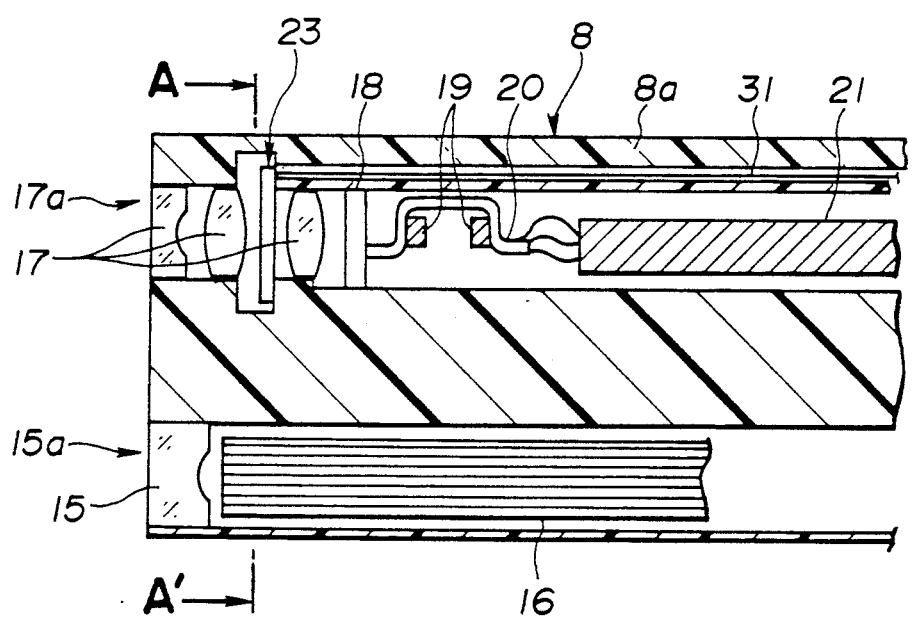
FIGS. 1 to 20 respectively illustrate a first embodiment of the present invention, where

As shown in FIG. 1, the above-described front portion 8 has an illuminating window 15a and an observation window 17a, the illuminating window 15a having an illuminating lens 15 on the inside thereof. A light guide 16 is disposed adjacent to the rear end portion of the illuminating lens 15, the light guide 16 being inserted into the insertion portion 2, the operation portion 3 and the universal cord 4. Thus, a light incidental end portion of the light guide 16 is connected to the above-described LG connector 5. In consequence, irradiating light emitted from the above-described light source device 40 can be made incident upon the incidental end portion of the light guide 16 so as be applied to the subject via the light guide 16 and the irradiating lens 15.

Furthermore, an objective lens group 17 serving as an objective optical system is disposed within the observing window 17a. In addition, a solid imaging device such as a CCD 18 is disposed at the imaging point of the above-described object lens group 17. A substrate 20 on which electronic parts 19 are mounted is connected to the CCD 18, and an electric signal line 21 is connected to the substrate 20. The signal line 21 is inserted into the insertion portion, the operation portion 3, the universal cord 4, the LG connector 5 and the CCU cable 6 so as to be connected to the CCU connector 7. Furthermore, the objective lens group 17 includes an iris diaphragm device 23.

Figure 2:
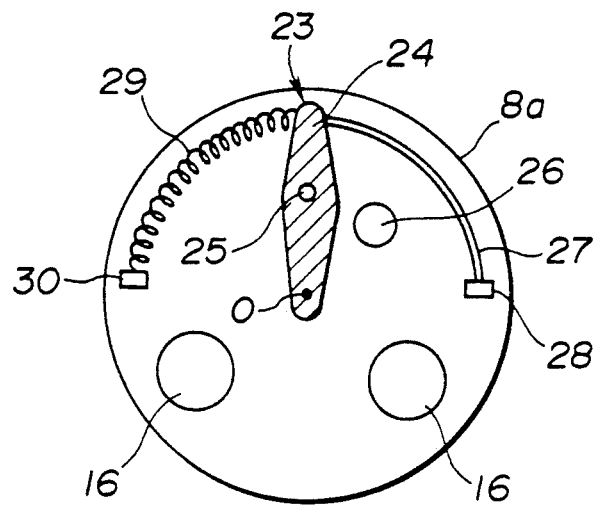
Figure 3:
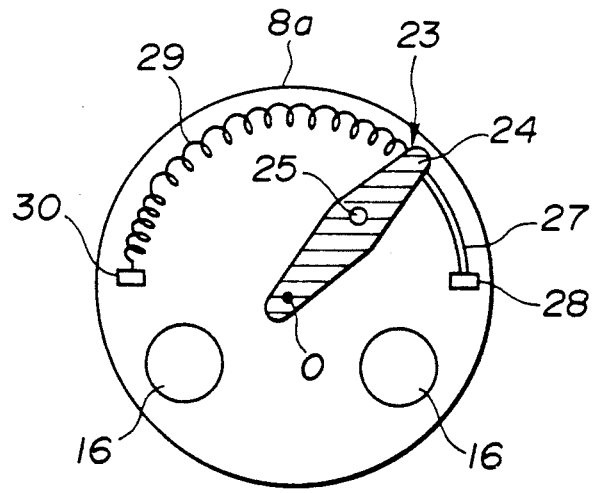

Then, a first embodiment of the above-described iris diaphragm device 23 will now be described with reference to FIGS. 2 and 3.

The iris diaphragm device 23 has an elongated aperture blade 24 as an iris diaphragm means, an end portion of the aperture blade 24 being rotatably fastened to a rotational shaft O positioned in the vicinity of the central axis of the insertion portion 2 in a main body 8a of the front portion 8 which serves as a base portion. Furthermore, the aperture blade 24 has a diaphragm aperture 25 at the central portion thereof. As a result, when the aperture blade 24 is rotated, the above-described diaphragm aperture 25 is placed or displaced from the optical path of the observing optical system 26 established by the objective lens group 17. An end portion of a shape-memory alloy 27 serving as a shape-memory material and an end portion of an elastic member 29 such as a spring are secured to the two side portions of another end portion of the aperture blade 24 by blazing or the like, the shape-memory alloy 27 and the elastic member 29 serving as operating means. Another end portion of the shape-memory alloy 27 and that of the elastic member 29 are secured to the main body 8a of the front portion 8 by securing members 28 and 30 at substantially symmetric positions with respect to the above-described rotational shaft O. The above-described shape-memory alloy 27 memorizes a contracted shape as shown in FIG. 3 in a hot phase (an asutenitic phase). An electric cable 31 is connected to the shape-memory alloy 27, the electric cable 31 being inserted into the insertion portion 2, the operation portion 3, the universal cord 4, the LG connector 5 and the CCU cable 6 so as to be connected to the CCU connector 7.

Figure 5:
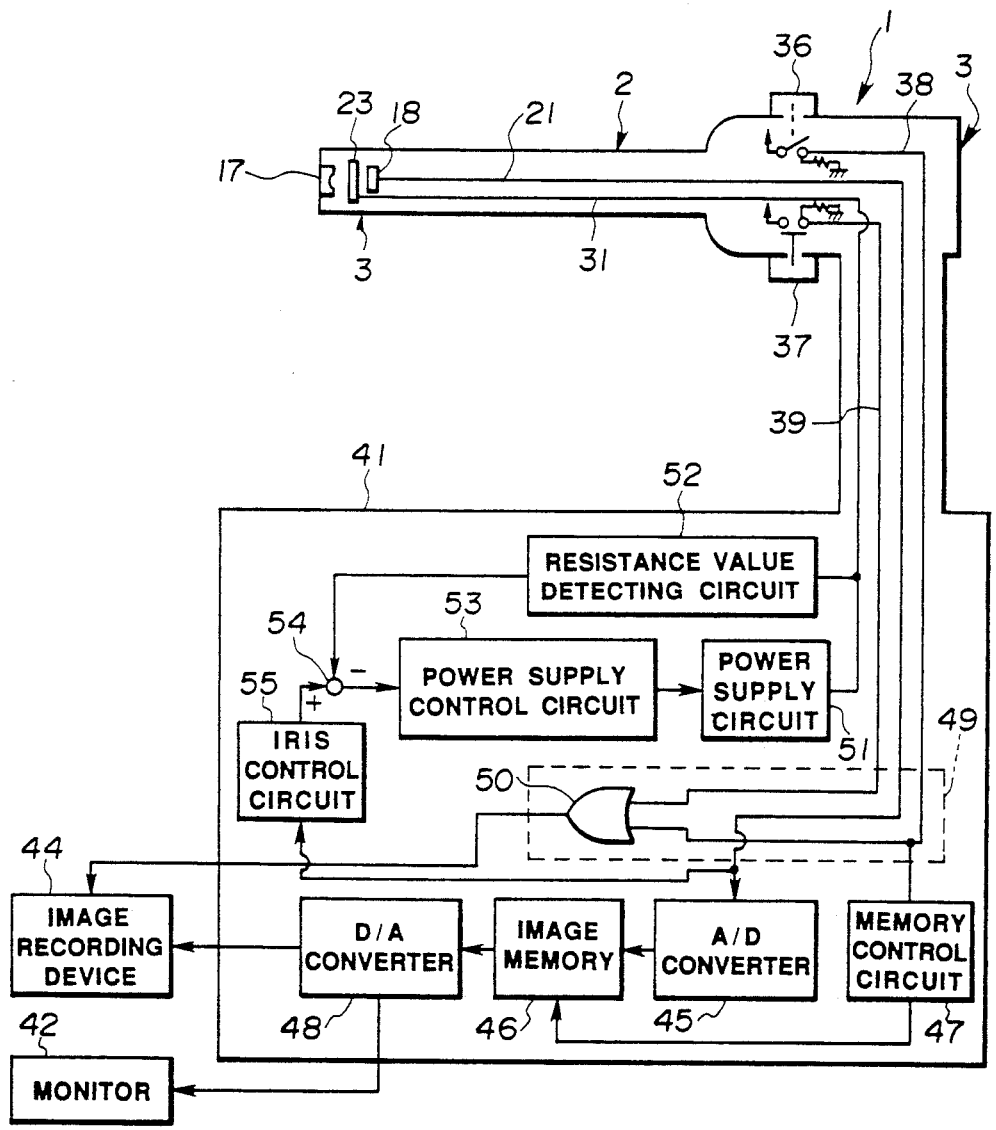
Figure 6:
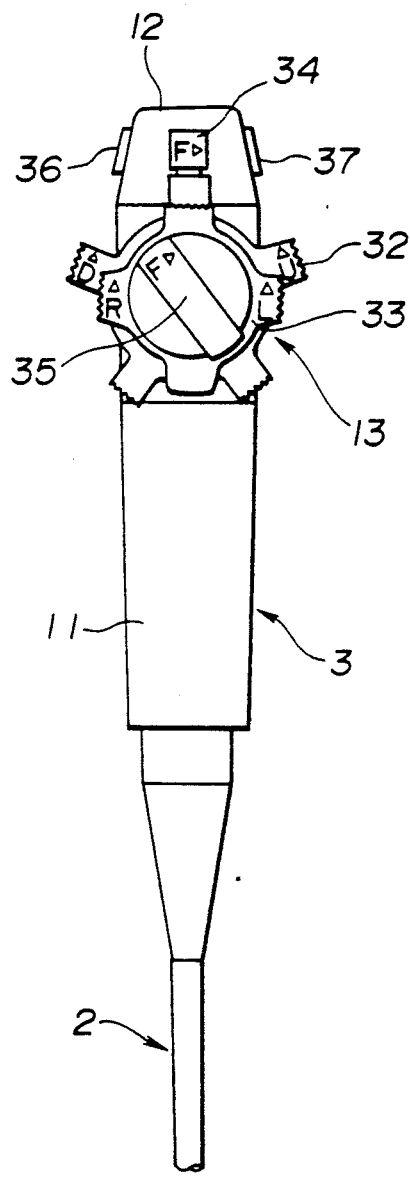

As shown in FIG. 6, the bending operation knob 13 disposed in the holding portion 11 of the operation portion 3 of the endoscope 1 is composed of a vertical bending operation knob 32, a lateral bending operation knob 33 and bending maintaining/cancelling knobs 34 and 35 for maintaining/cancelling the bent state realized by each of the knobs 32 and 33. On the other hand, the switch portion 12 has two operation switches, that is, an image fixing switch (to be abbreviated to an "FSW" hereinafter) 36 and an image recording switch (to be abbreviated to an "RSW" hereinafter) 37 at symmetric positions with respect to the lengthwise direction of the insertion portion 2. The FSW 36 comprises, for example, a push-button type toggle switch arranged in such a manner that, when it is once depressed by an operator, a state where the FSW 36 is switched on is maintained. When the FSW 36 is depressed again, it is switched off. The RSW 37 is switched on at the only moment when it is depressed. It is switched off when the finger of an operator is removed from the RSW 37. As shown in FIG. 5, a terminal of each of the FSW 36 and RSW 37 is connected to a power source, while another terminal of each of the same is connected to signal lines 38 or 39, furthermore the other terminals of the FSW 36 and RSW 37 being grounded via resistors. The signal lines 38 and 39 are inserted into the universal cord 4, the LG connector 5 and the CCU cable so as to be connected to the above-described CCU connector 7.

As shown in FIG. 5, the CCU 41 includes an A/D converter 45 connected to the CCD 18 via the signal line 21 and arranged to convert an analog video signal transmitted from the CCD 18 into a digital signal. An output signal from the A/D converter 45 is arranged to be received by the image memory 46. Signal writing and reading to and from the image memory 46 are controlled by a memory control circuit 47. Furthermore, the FSW 36 is connected to the memory control circuit 47 via the signal line 38. The output signal from the image memory 46 is converted into an analog signal by a D/A converter 48, the analog signal thus obtained being then transmitted to a monitor 42 disposed outside the CCU 41 and as well as transmitted to an image recording apparatus 44 In a case of a plane successive type structure in which irradiating light is successively switched over to light in wavelength regions R (red), G (green) and B (blue), the above-described image memory 46 is provided for each of images in the wavelength regions. The image signals in the corresponding wavelength regions are successively stored in the image memories 46. Then, the image signals in the corresponding wavelength regions are simultaneously read out from the image memories 46. In a case of a simultaneously type structure in which color separation is performed by a mosaic filter placed on the front source of the CCD 18, a circuit or the like for subjecting an output signal from the CCD 18 to the color separation process is disposed in front of the A/D converter 45.

The CCU 41 includes a switching detection portion 49 for controlling the image recording operation performed by the image recording device 44 in accordance with the state of the FSW 36 and the RSW 37. The switching detection portion 49 comprises, for example, an AND gate 50 having input terminals to which the FSW 36 and the RSW 37 are connected via the corresponding signal lines 38 and 39. The output from the AND gate 50 controls the image recording operation performed by the image recording device 44.

The CCU 41 includes a temperature controlling means included in a temperature changing means and composed of a power supply circuit 51 connected to the shape-memory alloy 27 via the cable 31, a resistance value detecting circuit 52, a power supply control circuit 53 for controlling the power supply circuit 51, an iris control circuit 55 for transmitting an aiming value for controlling the iris diaphragm device 23 disposed at the front portion 3 of the endoscope 1 and a subtracter 54 for subtracting an output from the resistance value detecting circuit 52 from the aiming value transmitted the iris control circuit 55 so as to transmit the result of the subtraction to the power supply control circuit 53 A video signal transmitted from the CCD 18 is arranged to be received by the iris control circuit 55.

Then, the operation of the iris diaphragm device 23 will now be described.

Irradiating light emitted from the light source device 40 is applied to the subject via the light guide 16 and the irradiating lens 15. The image of the subject irradiated with light is imaged on the CCD 18 by the objective lens group 17 so as to be photo-electrically converted. A signal transmitted from the CCD 18 is sequentially processed by the A/D converter 45, the image memory 46 and the D/A converter 48 so as to be transmitted to the monitor 42 or the image recording device 44.

The output signal from the CCD 18 is also transmitted to the iris diaphragm control circuit 55. The iris diaphragm control circuit 55 generates information about the brightness of the image of the subject in response to the output signal from the above-described CCD 18. In accordance with the brightness information thus generated, the iris diaphragm control circuit 55 transmits the aiming value which is used to control the iris diaphragm device 23. The aiming value is transmitted in the form of a resistance value which corresponds to the temperature of the shape-memory alloy 27 which is the means for operating the iris diaphragm device 23. The resistance value of the shape-memory alloy 27 is detected by the resistance value detecting circuit 52. The subtracter 54 subtracts the output from the resistance value detecting circuit 52 from the aiming value transmitted from the iris diaphragm control circuit 55, the result of the subtraction being then received by the power supply control circuit 53. The power supply control circuit 53 controls the power supply circuit 51 in accordance with the output from the subtracter 54 so as to control the quantity of power to be supplied from the power supply circuit 51 to the shape-memory alloy 27. The control of the power to be supplied may be performed in such a manner that the voltage is controlled or the electric current is controlled. As an alternative to this, the duty ratio may be changed by a pulse width modulation method. The shape-memory alloy to which the power is supplied through the power supply circuit 51 is heated and is contracted by a degree which corresponds to the quantity of the power supplied. Thus, the shape-memory alloy 27 is contracted to the designed state.

The iris diaphragm control circuit 55 does not command the power supply circuit 51 to supply power to the shape-memory alloy 27 if the quantity of light received by the CCD 18 is smaller than a predetermined quantity. In this case, the aperture blade 24 is, as shown in FIG. 2, placed at a position at which its diaphragm aperture 25 is retracted from the observing optical system 26 by the urging force of the elastic member 29, while the shape-memory alloy 27 is expanded. On the other hand, if the quantity of light received by the CCD 18 exceeds a predetermined level, the iris diaphragm control circuit 55 commands the power supply circuit 51 to supply power to the shape-memory alloy 27. In consequence, the shape-memory alloy 27 is contracted by the heat generated due to the supplied power in its lengthwise direction. As a result, the aperture blade 24 is moved against the urging force of the elastic member 29. Therefore, the diaphragm aperture 25 is, as shown in FIG. 3, moved to the central portion of the observing optical system 26. As a result, the quantity of light to be received by the CCD 18 is limited. When the power supply to the shape-memory alloy 27 is stopped, the aperture blade 24 is returned, by the urging force of the elastic member 29, to a position at which the diaphragm aperture 25 is retracted from the observing optical system 26 as shown in FIG. 2. If the quantity of light to be received by the CCD 18 is too large, the diameter of diaphragm aperture is reduced. In consequence, the quantity of incidental light is limited and the depth of field is enlarged. As an alternative to the above-described structure arranged in such a manner that the aperture blade 24 is automatically operated in accordance with the quantity of light to be applied to the CCD 18, another structure arranged in such a manner that the operation of the aperture blade 24 is commanded may be employed.

As described above, the iris diaphragm device 23 according to this embodiment is arranged in such a manner that the shape-memory alloy 27, which is deformed in accordance with the temperature, is employed as the means for displacing the aperture blade 24. Furthermore, the quantity of power to be supplied to the shape-memory alloy 27 is controlled so as to control the operation of the aperture blade 24. As a result, the structure of the mechanism for operating the aperture blade 24 can be simplified, the necessity of providing a transmission mechanism to be disposed between the aperture blade 24 and the operating means can be eliminated and the overall size of the iris diaphragm device 23 can be reduced. Therefore, the iris diaphragm device 23 can be accommodated in a small space such as the front portion 8 of the insertion portion 2 of the endoscope 1 in which it has been heretofore difficult for the iris diaphragm device 23 to be accommodated. Furthermore, the structure of the mechanism for operating the iris diaphragm device can be simplified, causing the size of the iris diaphragm device to be reduced. Therefore, the diameter of the front portion of the insertion portion of the endoscope can be reduced.

Figure 7:
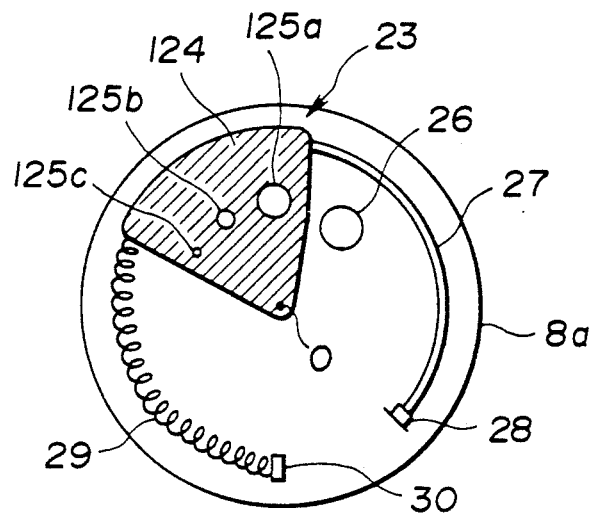

FIG. 7 illustrates a second embodiment of the iris diaphragm device according to the present invention.

The iris diaphragm device 23 according to this embodiment is arranged in such a manner that the elongated aperture blade 24 according to the first embodiment is replaced by a sectorial aperture blade 124. The central portion the sectorial aperture blade 124 is rotatably fastened to the rotational shaft O disposed in the vicinity of the central axis of the insertion portion 2. The above-described aperture blade 124 has three diaphragm apertures 125a, 125b and 125c having different sizes. In consequence, when the aperture blade 124 is rotated relative to the above-described rotational shaft O, the diaphragm apertures 125a, 125b and 125c are selectively placed on the optical path of the observing optical system 26 realized by the objective lens group 17. An end portion of the shape-memory alloy 27 serving as the shape-memory material and an end portion of the elastic member 29 such as a spring are secured to the two side portions of the outer surface of the aperture blade 124 by blazing or the like. Another end portion of the shape-memory alloy 27 and that of the elastic member 29 are secured to the main body 8a of the front portion 8 by securing members 28 and 30. Similarly to the first embodiment, the shape-memory alloy 27 memorizes a contracted shape in a hot phase (an asutenitic phase).

According to this embodiment, electrical energy to be supplied to the shape-memory alloy 27 is controlled in such a manner that the voltage is controlled or the electric current is controlled. In consequence, the overall length of the shape-memory alloy 27 is changed in a process in which the low temperature phase (martensite phase) is changed to a high temperature phase (austenitic phase). As a result, the plurality of the diaphragm apertures 125a, 125b and 125c having different sizes can selectively be moved to the observing optical system 26. As a result, the quantity of light can be finely adjusted.

The other structures, operations and the effects are the same as those according to the first embodiment.

Figure 8:
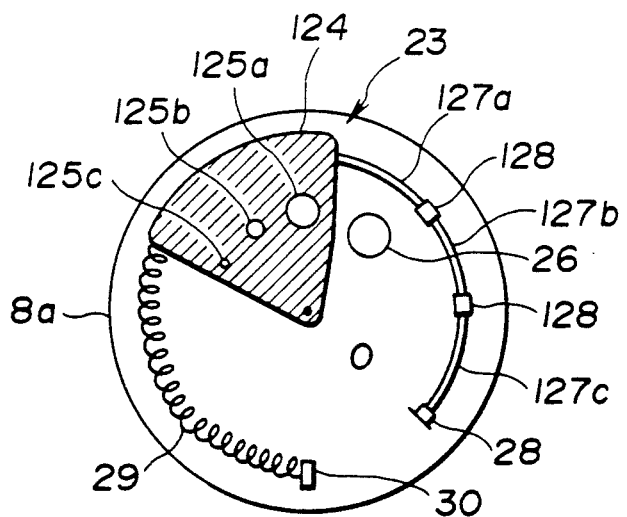

FIG. 8 illustrates a third embodiment of the iris diaphragm device according to the present invention.

The iris diaphragm device 23 according to this embodiment is arranged in such a manner that the shape-memory alloy 27 according to the second embodiment is replaced by three shape-memory alloys 127a, 127b and 127c serially connected in the axial direction via junctions 128. Each of the three shape-memory alloys 127a, 127b and 127c memorizes a contracted shape in the hot phase (austenitic phase). Therefore, the overall length can be changed by stages by changing the number of the shape-memory alloys 127a, 127b and 127c to which power is supplied.

According to this embodiment, when any one of the three shape-memory alloys 127a, 127b and 127c is supplied with power, the diaphragm aperture 125a is placed on the observing optical system 26. When two of the three shape-memory alloys 127a, 127b and 127c are supplied with power, the diaphragm aperture 125b is placed on the observing optical system 26. When all of the three shape-memory alloys 127a, 127b and 127c are supplied with power, the diaphragm aperture 125c is placed on the observing optical system 26. As described above, the three diaphragm apertures are optionally formed by changing the number of the shape-memory alloys to be supplied with power. Consequently, the quantity of light can finely be adjusted.

The other structures, operations and the effects are the same as those according to the first and second embodiments.

Figure 9:
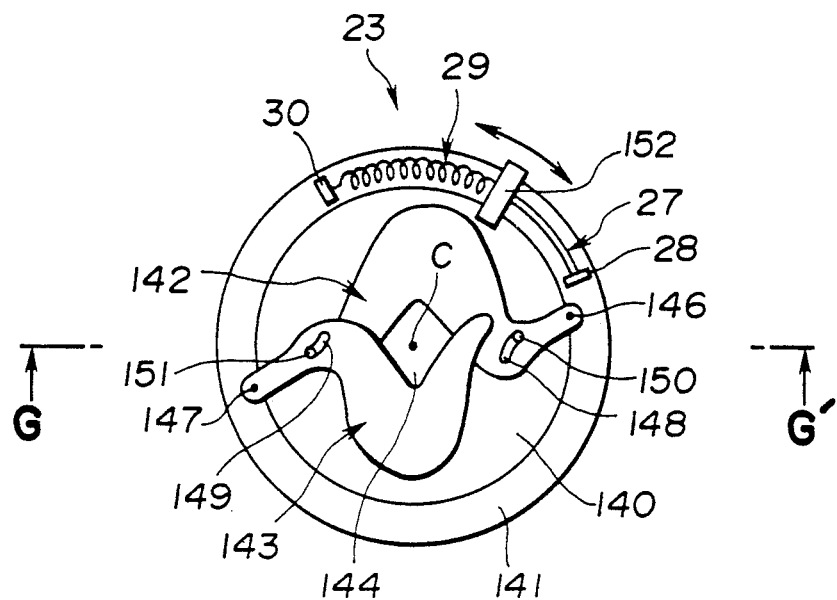
Figure 10:
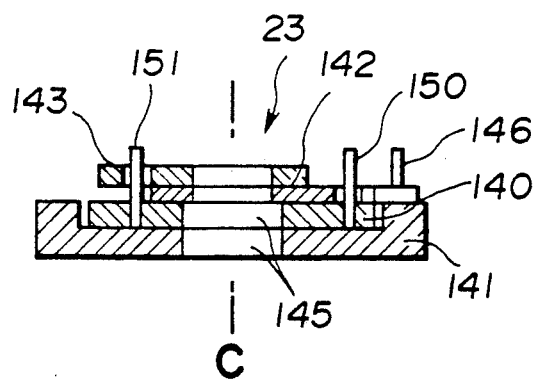

A fourth embodiment of the present invention will now be described with reference to FIGS. 9 and 10.

The iris diaphragm device 23 according to this embodiment comprises a disc-like base 141 having a circular iris diaphragm window 145 the center of which coincides with optical axis C of the observing optical system. The disc-like base 141 has, on either side thereof, a circular recessed portion the size of which is larger than that of the iris diaphragm window 145, the circular recessed portion rotatably accommodating a disc-like rotary member 140. Also the rotary member 140 has, at the central portion thereof, another window 145 the shape and the size of which are the same as the window 145 formed in the base 141. Pins 150 and 151 are elected from the surface of the rotary member 140 at symmetric positions with respect to the optical axis C, the pins 150 and 151 serving as projection portions. The rotary member 140 has a fixing knob 152 on the side surface of the rotary member 140. An end portion of the shape-memory alloy 27 and an end portion of the elastic member 29 such as a spring are, by, for example, blazing, secured to the two rotary directional end portions of the fixing knob 152. Another end portion of the shape-memory alloy 27 and another end portion of the elastic member 29 are respectively secured to the base 141 by the corresponding securing members 28 and 30. The shape-memory alloy 27 memorizes a contracted shape in a hot phase (austenitic phase) similarly to the first embodiment.

The iris diaphragm device 23 according to this embodiment comprises two aperture blades 142 and 143, each of the aperture blades 142 and 143 being secured to the base 141 by pins 146 and 147 at an end portion thereof. The aperture blades 142 and 143 have corresponding cam grooves 148 and 149 formed therein. The above-described pins 150 and 151 are fitted within the cam grooves 148 and 149. Consequently, when the rotary member 140 is rotated, the pins 150 and 151 are moved within the cam grooves 148 and 149 so that the aperture blades 142 and 143 are rotated relative to the pins 146 and 147. As a result of the movement of the aperture blades 142 and 143, a diaphragm aperture 144 is formed around the optical axis C, the size of the diaphragm aperture 144 being changed in accordance with the stages of the rotation of the aperture blades 142 and 143.

Then, the operation of this embodiment will now be described.

When power is supplied to the shape-memory alloy 27, the rotary member 140 rotates clockwise. At this time, the pins 150 and 151 secured to the rotary member 140 are moved within the cam grooves 148 and 149 formed in the aperture blades 142 and 143. As a result, the aperture blades 142 and 143 are rotated relative to the corresponding pins 146 and 147. In consequence, the size of the diaphragm aperture 144 is reduced. As described above, according to the present invention, the size of the diaphragm aperture 144 can be gradually controlled by controlling the quantity of power to be supplied to the shape-memory alloy 27.

The other structures, operations and the effects are the same as those according to the first and second embodiments.

Figure 11:
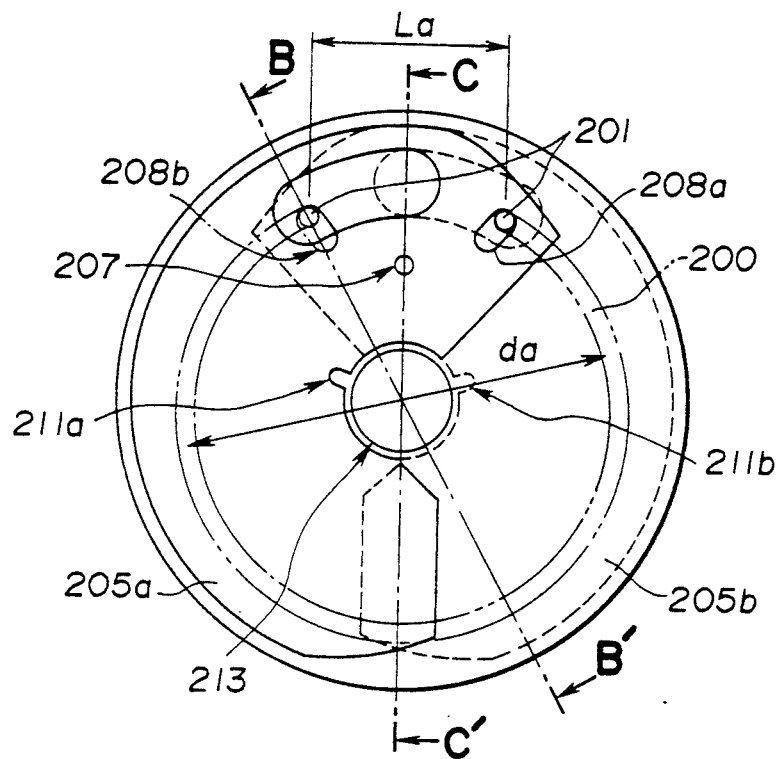
Figure 12:
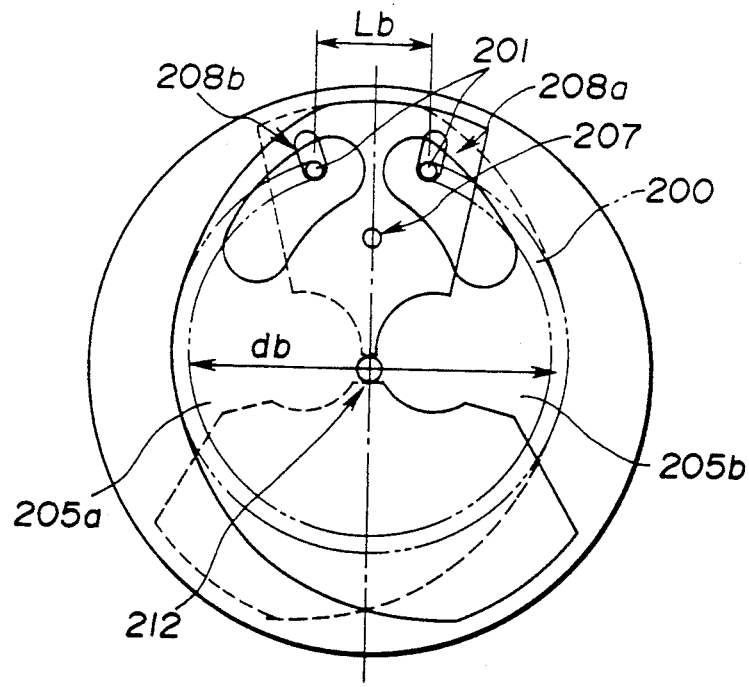
Figure 13:
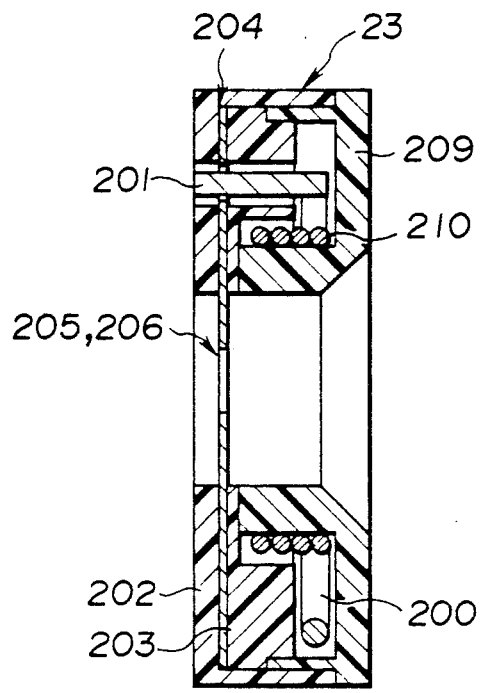
Figure 14:
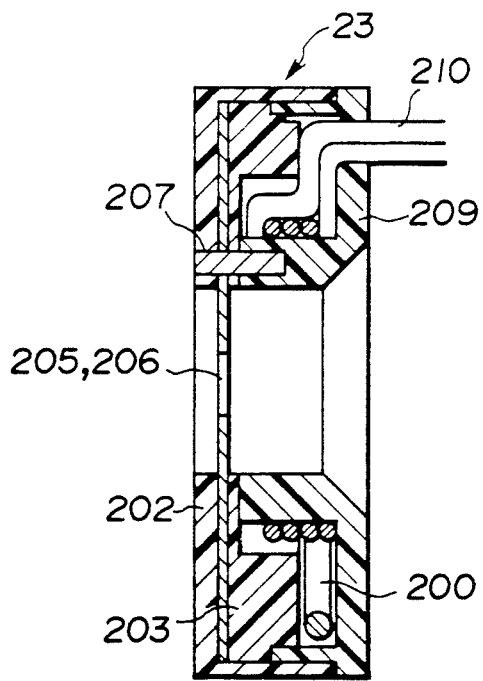
Figure 15:
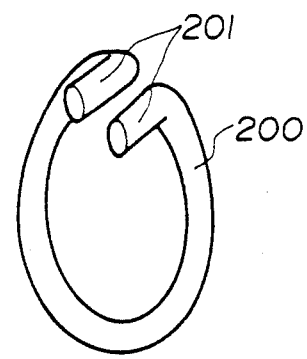
Figure 16:
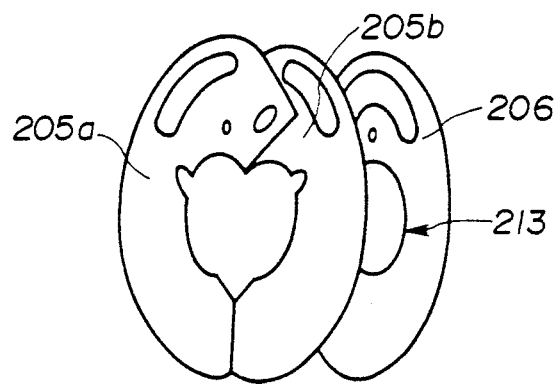

FIGS. 11 and 16 respectively illustrate a fifth embodiment of the present invention, where FIG. 11 is a front elevational view which illustrates a state where the diaphragm aperture of the iris diaphragm device is opened. FIG. 12 is a front elevational view which illustrates a state where a diaphragm aperture of the iris diaphragm device is opened. FIG. 13 is a cross sectional view taken along line B—B' of FIG. 11, FIG. 14 is a cross sectional view taken along line C—C' of FIG. 11, FIG. 15 illustrates a shape-memory alloy and FIG. 16 illustrates the configuration of aperture blades.

The iris diaphragm device 23 according to this embodiment comprises a base 209 having, at the central portion thereof, an annular projection portion formed in such a manner that a diaphragm window serving as the optical path of the observing optical system is formed. A nichrome wire 210 is wound around the annular projection portion of the base 209, the nichrome wire serving as a heating element. Furthermore, a shape-memory alloy 200 is positioned adjacently to the outer portion of the nichrome wire 210, the shape-memory alloy 200 serving as the operating member. The shape-memory alloy 200 is, as shown in FIG. 15, in the form of a C-figure the two end portions of which are in the form of projections 201 formed by rectangularly bending the two end portions. Furthermore, a stopper 203 is provided on the base 209 so as to prevent the lateral movement of the shape-memory alloy 200 when viewed in FIG. 13. In addition, a front cover 202 is fastened so as to cover the above-described elements. A space 204 in which a diaphragm blade 205 is rotated accommodates the aperture blade 205 and the iris diaphragm plate 206, the space 204 being formed between the front cover 202 and the stopper 203. As shown in FIG. 16, the aperture blade 205 comprises two aperture blades 205a and 205b, the aperture blade 205 being disposed in the space 204 in which the aperture blade 205 is rotated while being stacked on the iris diaphragm plate 206 having a large diaphragm aperture 213.

The apertures blades 205a and 205b are rotatably secured to the base 209 by a pin 207 which serves as a fixing shaft. The aperture blades 205a and 205b have corresponding cut portions 211a, 211b, cam grooves 208a and 208b. The projections 201 of the shape-memory alloy 200 are fitted within the cam grooves 208a and 208b. As a result, when the shape of the shape-memory alloy 200 is changed and the projections 201 are thereby moved within the cam grooves 208a and 208b, the aperture blades 205a and 205b are rotated relative to the pin 207. Since the above-described nichrome wire 210 is covered with an insulating material and is connected to the electric cable 31 shown in FIG. 1 so as to heat the shape-memory alloy 200 when power is supplied to the nichrome wire 210.

Then, the operation of the iris diaphragm device according to this embodiment will now be described.

The shape-memory alloy 200 is a two-way shape-memory alloy which memorizes the shape shown in FIG. 11 at room temperature in such a manner that the diameter of the C-shaped shape-memory alloy 200 is, for example, da. The shape-memory alloy 200 memorizes a shape formed due to a reduction of the diameter of the shape-memory alloy 200 from da to db as shown in FIG. 12, that is, the distance of the projections 201 from La to Lb when the shape-memory alloy 200 is heated to a level above a predetermined temperature by heat generated by the nichrome wire 210. Since the projections 201 of the shape-memory alloy 200 are placed within the corresponding cam grooves 208a and 208b of the aperture blades 205a and 205b, the aperture blades 205a and 205b are rotated relative to the pin 207 so as to be closed when the shape-memory alloy 200 is deformed as shown in FIG. 12 by heat generated by the nichrome wire 210 due to the supplied power. In consequence, a small diaphragm aperture 212 is formed by the cut portions 211a and 211b formed in the corresponding aperture blades 205a and 205b.

When the power supply to the nichrome wire 210 is stopped, the temperature is lowered due to heat radiation, causing the shape of the C-shaped shape-memory alloy 200 to be changed from that FIG. 12 to the shape shown FIG. 11. As a result, the aperture blades 205a and 205b are opened so that a large diaphragm aperture 213 is formed by the iris diaphragm plate 206.

As described above, according to this embodiment, two types of diaphragm apertures can be formed by supplying/stopping the supply of the power to the nichrome wire 210. Therefore, the quantity of light to be made incident upon a solid-state image sensing device or the like can be adjusted. Furthermore, since the two-way shape-memory alloy is employed, the necessity of using a restoring spring can be eliminated.

The other structures, operations and the effects are the same as those according to the first and second embodiments.

Figure 17:
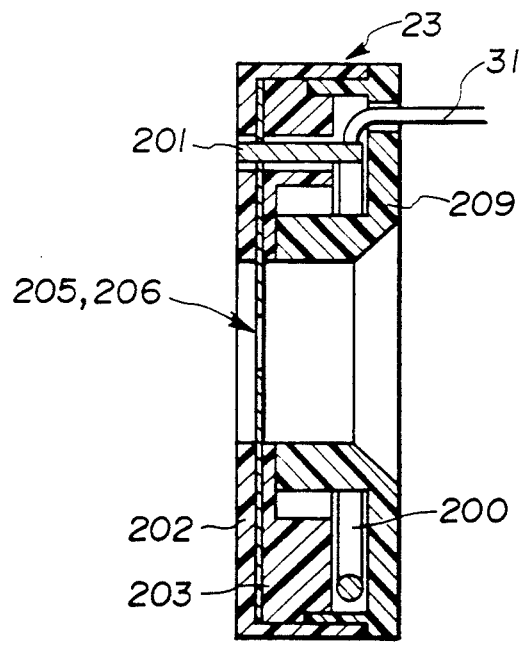

FIG. 17 is a cross sectional view which illustrates a sixth embodiment of the iris diaphragm device according to the present invention, the sixth embodiment being a modification to the fifth embodiment. FIG. 17 is a cross sectional view taken along line B—B' of FIG. 11.

According to this embodiment, an electric cable 31 is, by, for example, pressure, directly electrically connected to the shape-memory alloy 200. The front cover 202, the stopper 203 and the base 209 and the like are formed by polycarbonate in order to realize insulation. The other structure are the same as those according to the fifth embodiment.

According to this embodiment, the shape-memory alloy 200 is directly heated without the nichrome wire 210. Therefore, the responsibility of the change in the diameter of the diaphragm aperture can be improved.

The other operations and effects are the same as those obtainable from the fifth embodiment.

Figure 18:
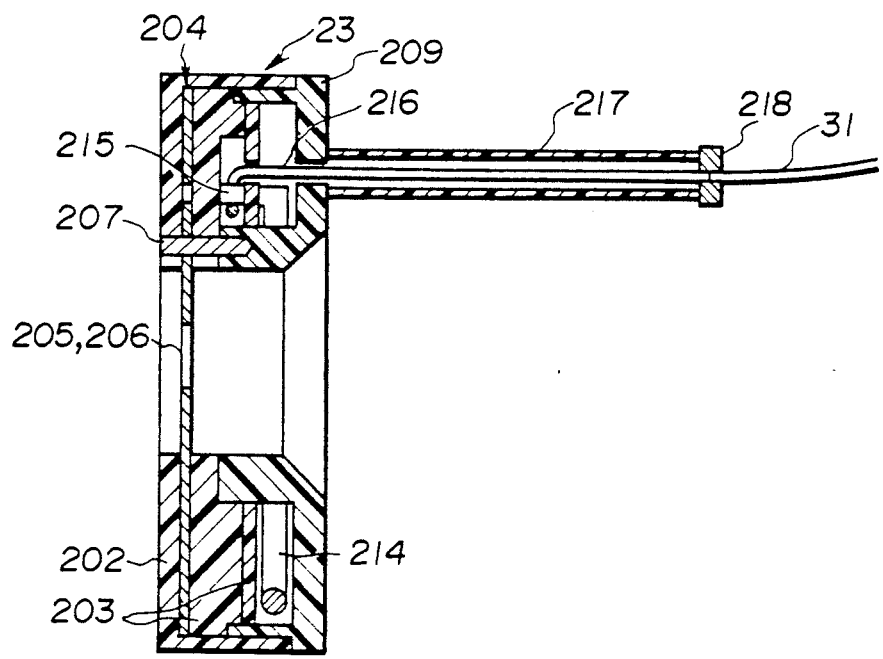
Figure 19A:
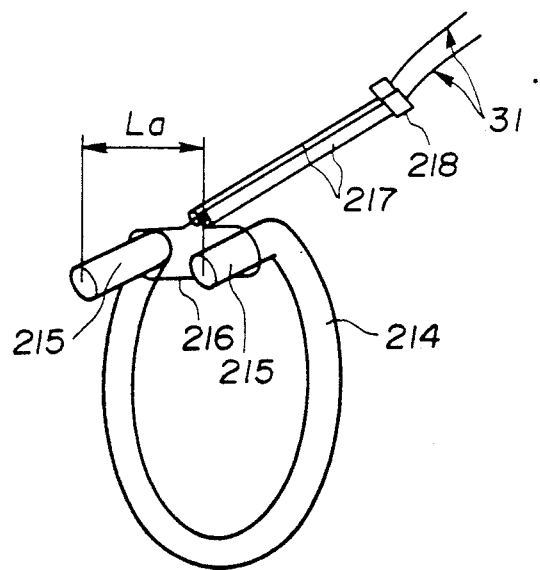
Figure 19B:
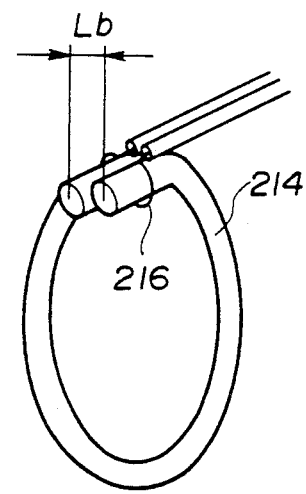

FIGS. 18 and 19 illustrate a seventh embodiment of the present invention, where FIG. 18 is a cross sectional view which illustrates the iris diaphragm device and FIG. 19 illustrates the relationship between the operation of a restoring spring and a that of shape-memory alloy wire (to be abbreviated to an "SMA wire" hereinafter).

According to this embodiment, the shape-memory alloy 200 according to the fifth and sixth embodiments serving as the operating member is replaced by a restoring spring 214 employed as a C-shaped elastic member which is covered with an insulating material. An SMA wire 216 capable of extending/contracting in its axial direction due to the change in temperature is arranged between two projections 215 formed on the restoring spring 214. As shown in FIG. 19, the SMA wire 216 has a circular fastening portion to fasten the projections 215 of the restoring spring 214. Consequently, the restoring force of the restoring spring 214 in the direction in which the diameter of it is enlarged can be restricted. The two end portions of the SMA wire 216 are inserted into pipes 217 respectively coated with insulating materials or made of insulating materials so as to be, together with the electric cable 31, secured by a crimp-style terminal 218 having a size larger than the inner diameter of the pipe 217. Also according to this embodiment, the front cover 202, the stopper 203, the base 209 and the like are formed by, for example, polycarbonate for the purpose of realizing an insulation.

The SMA wire 216 is contracted in its axial direction when it is heated to a level exceeding a predetermined temperature, while the original length is restored when the temperature is lowered. When the SMA wire 216 is heated by supplied electricity, the SMA wire 216 is contracted as shown in FIG. 19. Consequently, the restoring spring 214 is deformed in such a manner that the distance between the projections 215 of the restoring spring 214 is reduced from La to Lb since the two end portions of the SMA wire 216 are secured at the end portions of the pipes 217. When the supply of power to raise the temperature of the SMA wire 216 is stopped, the temperature of the SMA wire 216 is lowered due to heat radiation. As a result, the original length of the SMA wire 216 is, as shown in FIG. 19A, restored so that the original shape of the restoring spring 214 is restored.

As described above, the shape of the restoring spring 214 is changed by extending/contracting the SMA wire 216. Hence, a plurality of sizes of the diaphragm aperture can be realized by rotating the aperture blade. Consequently, the quantity of light to be made incident upon the solid-state image sensing device can be adjusted.

The other structures, operations and effects are the same as those obtainable from the fifth embodiment.

Figure 20:
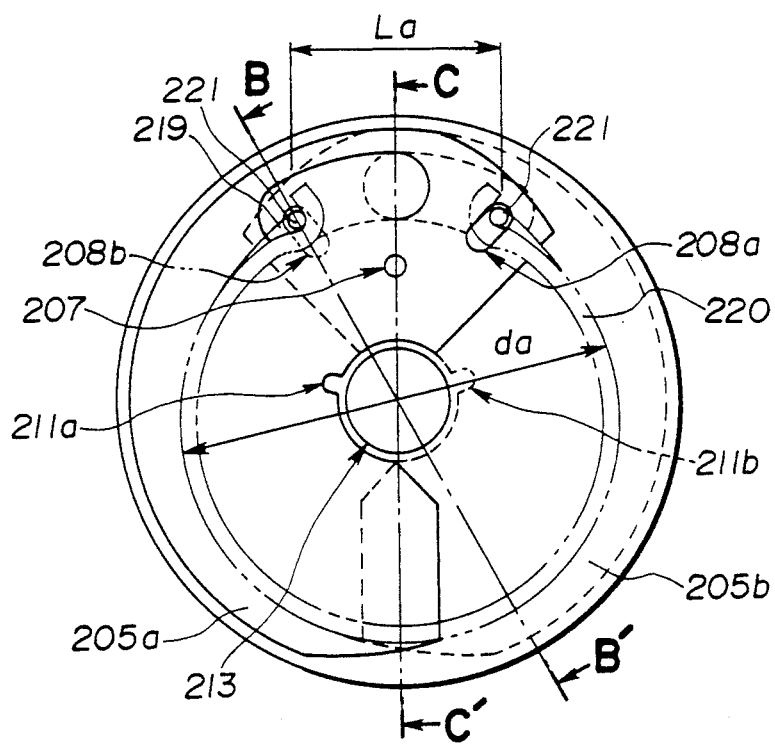
Figure 21:
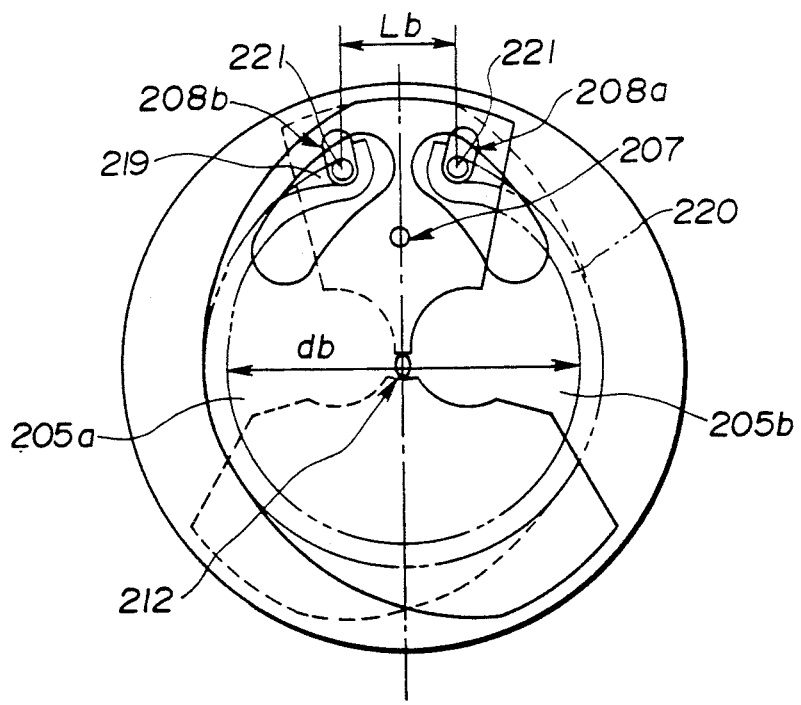
Figure 22:
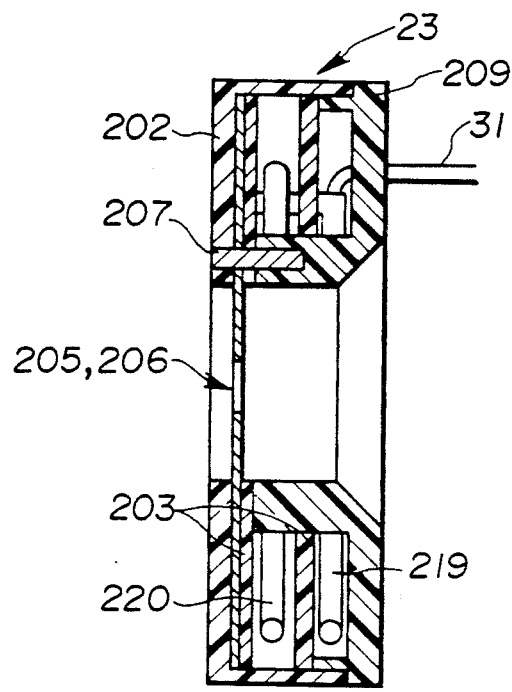
Figure 23:
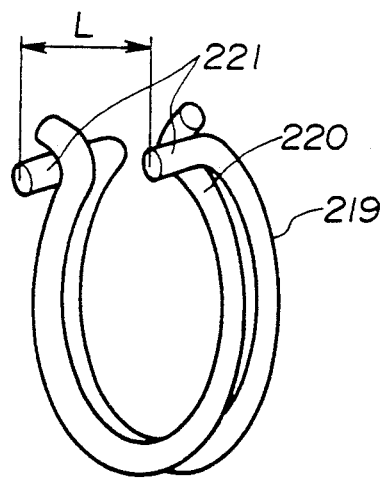

FIGS. 20 to 23 respectively illustrate an eighth embodiment of the present invention, where FIG. 20 is a front elevational view which illustrates a state where a diaphragm aperture of an iris diaphragm device is opened. FIG. 21 is a front elevational view which illustrates a state where the diaphragm aperture of the iris diaphragm device is closed. FIG. 22 is a cross sectional view taken along line C—C' of FIG. 20. FIG. 23 illustrates the relationship between the shape-memory alloy and the restoring spring shown in FIG. 20.

As shown in FIGS. 20 to 22, according to this embodiment, the two-way shape-memory alloy 200 according to the sixth embodiment as the operation member is replaced by one-way shape-memory alloy 219 and a restoring spring 220 is employed as the elastic member. The shape-memory alloy 219 and the restoring spring 220 are disposed in such a manner that distance L between two projections 221 of the shape-memory alloy 219 is, as shown in FIG. 23, enlarged by the urging force of the C-shaped restoring spring 220.

The shape-memory alloy 219 memorizes a shape formed due to a reduction of the diameter of the restoring spring 220 from da to db as shown in FIGS. 20 and 21, that is, the distance of the projections 221 from La to Lb when the shape-memory alloy 219 is heated to a level above a predetermined temperature by the supplied power. Since the shape-memory alloy 219 is a one-way type shape-memory alloy, a certain memorized shape is kept at high temperatures. However, it the temperature is lowered below a predetermined level, the original shape is restored by external force.

According to this embodiment, when the power supply to the shape-memory alloy 219 is stopped, the temperature is lowered due to heat radiation, causing the shape of the shape-memory alloy 219 to be deformed from that shown in FIG. 21 to the shape shown in FIG. 20 by the restoring spring 220 As a result, since the aperture blades 205a and 205b are rotated, a plurality of sizes of the diaphragm aperture can be obtained. Therefore, the quantity of light to be made incident upon the solid-state image sensing device or the like can be adjusted.

The other structures, operations and the effects are the same as those according to the fifth embodiment.

The present invention is not limited to the above-described embodiments. For example, the shape-memory alloy serving as the operating means to displace the aperture blade is not limited to the shape-memory alloy which can be contracted/expanded. It may be a shape-memory alloy which can be bent so as to change the size of the diaphragm aperture formed in the aperture blade. Furthermore, a shape-memory resin may be employed as an alternative to the shape-memory alloy.

Furthermore, the necessity of individually providing the aperture blade and the operating means for displacing the aperture blade can be eliminated. Another structure may be employed which is arranged in such a manner that the aperture blade is deformed by the electricity supplied to the shape-memory alloy so that the size of the diaphragm aperture is changed.

The present invention is not limited to the iris diaphragm device which is included in the observing optical system disposed at the front portion of the insertion portion of the endoscope. It may be included in an irradiating optical system disposed at the front portion or in the light source device.

The present invention may be applied to both medical endoscopes and industrial endoscopes.

The present invention may be applied to optical endoscopes such as fiber scopes as well as the above-described electronic endoscope. Furthermore, the same may be applied to both soft scopes and hard scopes.

In addition, the present invention may be applied to an iris diaphragm device for a light source devices or imaging devices as well as the endoscopes.

Although the invention has been described in its preferred form with a certain degree of particularly, it is understood that the present disclosure of the preferred form has been changed in the details of construction and the combination and arrangement of parts may be resorted to without departing from the spirit and the scope of the invention as hereinafter claimed.

What is claimed is:

1. An iris diaphragm device comprising:
   iris diaphragm means which is displaced so as to change the diameter of a diaphragm aperture;
   operating means including a shape-memory material which is deformed in accordance with temperatures, so as to displace said iris diaphragm means; and
   temperature changing means for changing the temperature of said shape-memory material of said operating means.

2. An iris diaphragm device comprising:
   an objective optical system for imaging incidental light beams;
   iris diaphragm means which is disposed on the optical path of said objective optical system and which is displaced, so as to change the diameter of a diaphragm aperture;
   operating means including a shape-memory material which is deformed in accordance with temperatures, so as to displace said iris diaphragm means; and
   temperature changing means for changing the temperature of said shape-memory material of said operating means.

3. An iris diaphragm device according to claim 1 or 2, wherein said shape-memory material is a shape-memory alloy.

4. An iris diaphragm device according to claim 1 or 2, wherein said shape-memory is a shape-memory alloy and said temperature changing means has a temperature control means for controlling the temperature of said shape-memory alloy, said temperature changing means being directly electrically connected to said shape-memory alloy.

5. An iris diaphragm device according to claim 1 or 2, wherein said temperature changing means includes a heating element for heating said shape-memory material, said heating element being disposed adjacently to said shape-memory device.

6. An iris diaphragm device according to claim 1 or 2, wherein said shape-memory material is a one-way type shape-memory material which memorizes a shape in a low temperature phase or a high temperature phase.

7. An iris diaphragm device according to claim 1 or 2, wherein said shape-memory material is a two-way type shape-memory material which memorizes two shapes in a low temperature phase and a high temperature phase.

8. An iris diaphragm device according to claim 1 or 2, wherein said iris diaphragm means includes a base having a diaphragm window formed therein and a diaphragm blade having a diaphragm aperture having a size different from said iris diaphragm window, an end portion of said aperture blade being rotatably secured to said base by a fixing shaft.

9. An iris diaphragm device according to claim 1 or 2, wherein said iris diaphragm means includes:
   a base having a diaphragm window formed therein; and
   a diaphragm blade having a diaphragm aperture having a size different from said iris diaphragm window, an end portion of said aperture blade being rotatably secured to said base by a fixing shaft, and said operating means includes:
      an elongated shape-memory material an end portion of which is secured to said base and another end portion of the same is secured to an end portion of said aperture blade on the opposite side to said fixing shaft, said elongated shape-memory material being deformed in accordance with temperatures; and
      an elastic member an end portion of which is secured to said base and another end portion of the same is secured to an end portion of said aperture blade on the opposite side to said fixing shaft in such a manner that said elastic member confronts said shape-memory material.

10. An iris diaphragm device according to claim 9, wherein said aperture blade has an elongated diaphragm aperture formed therein.

11. An iris diaphragm device according to claim 9, wherein said aperture blade is in the form of a sector having a plurality of diaphragm apertures having different sizes.

12. An iris diaphragm device according to claim 9, wherein said aperture blade is in the form of a sector having a plurality of diaphragm apertures having different sizes and said shape-memory material of said operating means is formed by serially connecting a plurality of materials in the axis direction, said plurality of materials being respectively independently connected to said temperature changing means.

13. An iris diaphragm device according to claim 1 or 2, wherein said iris diaphragm means includes:
   a base having a circular iris diaphragm window formed in the central portion thereof; and
   a plurality of aperture blades rotatably secured to said base by a fixing shape, said plurality of aperture blades forming a diaphragm aperture at the central portion of said base.

14. An iris diaphragm device according to claim 1 or 2, wherein said iris diaphragm means includes:
   a disc-like base having a circular iris diaphragm window at the central portion thereof and a recessed portion the diameter of which is larger than that of said iris diaphragm window; and
   two aperture blades having elongated cam grooves and rotatably secured to the periphery of said base by fixing shafts so as to form a diaphragm aperture at the central portion of said base, and
   said operating means includes:

a rotary member having two projections which are respectively fitted within said cam grooves so as to displace said aperture blades and a fixing knob formed on the periphery thereof, said rotary member being rotatably placed in said recessed portion of said base;

an elongated shape-memory material an end portion of which is secured to said fixing knob and another end portion of which is secured to the periphery of said base, said elongated shape-memory material being deformed in its lengthwise direction in accordance with temperatures; and an elastic member an end portion of which is secured to said fixing knob so as to confront said shape-memory material and another end portion of which is secured to the periphery of said base.

15. An iris diaphragm device according to claim 1 or 2, wherein said iris diaphragm means includes:

a base having, at the central portion thereof, an annular projection for forming a diaphragm window;

a stopper for covering a portion between the outer periphery of said base and said annular projection; and two aperture blades having elongated cam grooves, rotatably secured on said base by fixing shafts so as to form a diaphragm aperture at the central portion of said base, and said operating means has:

an operating member which is disposed between a space formed by said annular projection and said stopper and which is fitted within said cam grooves of said aperture blades so as to displace said aperture blades in accordance with temperatures.

16. An iris diaphragm device according to claim 1 or 2, wherein said iris diaphragm means includes:

a base having, at the central portion thereof, an annular projection for forming a diaphragm window;

a stopper for covering a portion between the outer periphery of said base and said annular projection; and two aperture blades having elongated cam grooves, rotatably secured on said base by fixing shafts so as to form a diaphragm aperture at the central portion of said base, said operating means has:

an operating member which is disposed between a space formed by said annular projection and said stopper and which is fitted within said cam grooves of said aperture blades so as to displace said aperture blades in accordance with temperatures, and said temperature changing means includes a heating element wound around said annular projection portion so as to heat said operating member.

17. An iris diaphragm device according to claim 15, wherein said operating member includes a shape-memory alloy which is deformed in accordance with temperatures, said operating member being directly electrically connected to said temperature control means disposed in said temperature changing means, said temperature control means controlling the temperature of said shape-memory alloy.

18. An iris diaphragm device according to claim 15 wherein said operating member is constituted by a C-shaped shape-memory material having projections which are fitted within said cam grooves formed in said aperture blades.

19. An iris diaphragm device according to claim 15, wherein said operating member includes a C-shaped elastic material having projections which are fitted within said cam grooves formed in said aperture blades, and a shape-memory alloy wire which is expanded/contracted in the axial direction in accordance with temperatures, which is arranged between said projections so as to restrict restoring force of said elastic member and two end portions of which are secured.

20. An iris diaphragm device according to claim 15, wherein said operating member includes a C-shaped shape-memory material having projections which are fitted within said cam grooves formed in said aperture blades and elastic members which are fastened to said projections of said shape-memory material and which urge said shape-memory material in a direction in which the distance between said projections is elongated.

21. An endoscope comprising:

a holding portion disposed adjacent to an operator;

an elongated insertion portion extending in front of said holding portion;

an objective optical system disposed at the front portion of said insertion portion and arranged to image incidental light beams;

an iris diaphragm device including iris diaphragm means which is disposed on the optical path of said objective optical system and which is deformed so as to change the diameter of a diaphragm aperture and operating means having a shape-memory material which is deformed in accordance with temperatures so as to displace said iris diaphragm means; and temperature control means for controlling the temperature of said shape-memory material.

22. An endoscope comprising:

a holding portion disposed adjacent on an operator;

an elongated insertion portion extending in front of said holding portion;

an objective optical system disposed at the front portion of said insertion portion and arranged to image incidental light beams;

an iris diaphragm device including iris diaphragm means which is disposed on the optical path of said objective optical system and which is deformed so as to change the diameter of a diaphragm aperture, operating means having a shape-memory material which is deformed in accordance with temperatures so as to displace said iris diaphragm means and an heating element for heating said shape-memory material of said operating means; and temperature control means for controlling said heating element.

23. An endoscope according to claim 21 or 22, wherein said shape-memory material of said iris diaphragm device is a shape-memory alloy.

24. An endoscope according to claim 21, wherein said shape-memory material of said iris diaphragm device is a shape-memory alloy and said temperature control means is directly electrically connected to said shape-memory alloy.

25. An endoscope according to claim 22, wherein said heating element is disposed adjacently to said shape-memory material.

26. An endoscope according to claim 21 or 22, wherein said iris diaphragm means provided for said iris diaphragm device includes a base having a diaphragm window and a diaphragm blade having a diaphragm aperture the size of which is different from that of said iris diaphragm window, and end of said aperture blade being rotatably secured to said base by a fixing shaft.

27. An endoscope according to claim 21 or 22, wherein said iris diaphragm means includes a base having a diaphragm window at the central portion thereof and a plurality of aperture blades which are rotatably secured to said base by a fixing shaft and which form a diaphragm aperture at the central portion of said base.

* * * * *